United States Patent
Matsui et al.

(10) Patent No.: US 10,328,004 B2
(45) Date of Patent: Jun. 25, 2019

(54) SUNSCREEN COSMETIC

(71) Applicant: SHISEIDO COMPANY, LTD., Tokyo (JP)

(72) Inventors: Takashi Matsui, Kanagawa (JP); Taichi Harada, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/762,452

(22) PCT Filed: Sep. 30, 2016

(86) PCT No.: PCT/JP2016/079012
§ 371 (c)(1),
(2) Date: Mar. 22, 2018

(87) PCT Pub. No.: WO2017/057677
PCT Pub. Date: Apr. 6, 2017

(65) Prior Publication Data
US 2018/0296452 A1    Oct. 18, 2018

(30) Foreign Application Priority Data

Sep. 30, 2015 (JP) .................. 2015-194664
Apr. 7, 2016 (JP) .................. 2016-077552

(51) Int. Cl.
*A61K 8/35* (2006.01)
*A61K 8/37* (2006.01)
*A61K 8/27* (2006.01)
*A61K 8/29* (2006.01)
*A61Q 17/04* (2006.01)
*A61K 8/41* (2006.01)
*A61K 8/49* (2006.01)

(52) U.S. Cl.
CPC .................. *A61K 8/37* (2013.01); *A61K 8/27* (2013.01); *A61K 8/29* (2013.01); *A61K 8/35* (2013.01); *A61K 8/415* (2013.01); *A61K 8/4966* (2013.01); *A61Q 17/04* (2013.01); *A61K 2800/30* (2013.01)

(58) Field of Classification Search
None
See application file for complete search history.

(56) References Cited

U.S. PATENT DOCUMENTS

| | | | | |
|---|---|---|---|---|
| 2015/0010601 A1* | 1/2015 | Roudot | ................... | A61K 8/25 424/401 |
| 2015/0216766 A1* | 8/2015 | Tanaka | ................... | A61Q 17/04 424/401 |

FOREIGN PATENT DOCUMENTS

| | | |
|---|---|---|
| EP | 1 555 015 | 7/2005 |
| EP | 2 092 928 | 8/2009 |
| JP | 3491933 | 4/1995 |
| JP | 3683533 | 7/2003 |
| JP | 2008-162988 | 7/2008 |
| JP | 2013-199451 | 10/2013 |
| JP | 2014114273 | 6/2014 |
| JP | 2014-205628 | 10/2014 |
| JP | 2014-240382 | 12/2014 |
| JP | 2013-505548 | 2/2015 |
| JP | 2015-044879 | 3/2015 |
| JP | 2015-509925 | 4/2015 |
| JP | 2015-120682 | 7/2015 |
| JP | 2015-124172 | 7/2015 |
| WO | WO 2007/122822 | 11/2007 |
| WO | WO 2011/136121 | 11/2011 |
| WO | WO 2011/155404 | 12/2011 |

OTHER PUBLICATIONS

PCT/JP2016/079012, International Search Report and Written Opinion, dated Oct. 25, 2016, 2 pages—English, 8 pages—Japanese.
Japanese Patent No. 6143914 (from PCT), Reasons for Revocation dated Feb. 9, 2018, 4 pages—Japanese, 2 pages—English.
Japanese Patent No. 614914, 'Corrected Claims' for allowance following refocation filing, 1 page—English.
EP 16851846.2, Extended European Search Report dated Mar. 14, 2019, 8 pages—English.

* cited by examiner

*Primary Examiner* — Nannette Holloman
(74) *Attorney, Agent, or Firm* — Andrew F. Young, Esq.; Lackenbach Siegel, LLP

(57) ABSTRACT

A sunscreen cosmetic achieves high ultraviolet ray protection effect even when restricting a blended amount of the liquid ultraviolet ray absorbing agents ethylhexyl methoxycinnamate and octocrylene, that is stable and has excellent texture, and does not resulting in an unnatural whiteness on application. A sunscreen cosmetic comprises: (A) 0.5 to 10.0 mass % of t-butyl methoxydibenzoylmethane and/or diethylamino hydroxybenzoyl hexyl benzoate; (B) 0.5 to 5.0 mass % of bis-ethylhexyloxyphenol methoxyphenyl triazine; (C) 0.5 to 5.0 mass % of ethylhexyl triazone; (D) 5 to 50 mass % of an ester oil to which the ingredients (A), (B) and (C) have a solubility, at 25° C., of 10% or more; and (E) 1.5 to 12 mass % of an ultraviolet ray scattering agent; wherein the total blended amount of the ingredients (A), (B) and (C) is 1.5 to 15 mass % and the total blended amount of ethylhexyl methoxycinnamate and octocrylene is 3 mass % or less.

5 Claims, No Drawings

SUNSCREEN COSMETIC

CROSS REFERENCE TO RELATED APPLICATIONS

This application relates to and claims priority as a § 371 national phase, from PCT/JP2016/079012 FILED Sep. 30, 2016, the entire contents of which are incorporated herein by reference, which in turn claims priority from JP 2016-077552 filed Apr. 7, 2016 and from JP 2015-194664 filed Sep. 30, 2015

TECHNICAL FIELD

The present invention relates to a sunscreen cosmetic. More specifically, the present invention relates to a sunscreen cosmetic that has excellent stability and that achieves high ultraviolet ray protection performance across a wide wavelength range from UVA to UVB, even when the blended amount of an ultraviolet ray absorbing agent is reduced from the amount that has conventionally been generally used.

BACKGROUND ART

Protecting the skin from damage due to ultraviolet rays is an important object in skin care and body care, and various UV-care cosmetics for minimizing the harmful effects of ultraviolet rays on the skin have been developed. Sunscreen cosmetics, which are a type of UV-care cosmetic, are cosmetics that are intended to protect the skin from damage due to ultraviolet rays, by covering the skin with a coating that contains an ultraviolet ray absorbing agent or an ultraviolet ray scattering agent, thereby absorbing or scattering UVA and UVB rays, and limiting the amount of ultraviolet rays that reach the skin (Non-Patent Document 1).

Ethylhexyl methoxycinnamate and octocrylene (2-ethylhexyl 2-cyano-3,3-diphenylprop-2-enoate) have been generally used in conventional sunscreen cosmetics, as liquid ultraviolet ray absorbing agents having absorption wavelengths primarily in the UVB range. However, these ultraviolet ray absorbing agents can sometimes irritate the skin of users with sensitive skin, and for example, a skin-care preparation for external use in which irritation due to ethylhexyl methoxycinnamate is mitigated by adding polypropylene glycol dimethyl ether has been proposed (Patent Document 1).

Patent Document 2 discloses a so-called non-chemical sunscreen cosmetic that does not contain ethylhexyl methoxycinnamate, octocrylene or avobenzone, but instead contains a combination of multiple powder ingredients that have an ultraviolet ray scattering effect, and the cosmetic does not irritate the eyes even when applied to the face. However, it is necessary to add a large quantity of powder ingredients in order to obtain high ultraviolet ray protection effects (high SPF) using only powder ingredients, and in some cases, an unnatural whiteness can occur when applied to the skin.

On the other hand, most organic ultraviolet ray absorbing agents other than ethylhexyl methoxycinnamate and octocrylene are solid at ambient temperature. In conventional sunscreen cosmetics, liquid ethylhexyl methoxycinnamate and octocrylene also served the function of solvents, so there were no problems. However, if the blended amounts of these liquid ultraviolet ray absorbing agents are reduced, the co-blended solid ultraviolet ray absorbing agents can sometimes precipitate out, and if the blended amounts of the solvents (oils) used for the solid ultraviolet ray absorbing agents are increased in order to prevent precipitation, then the blending ratio of the ultraviolet ray absorbing agents relative to the entire cosmetic decreases, so that sufficient ultraviolet ray protection effects cannot be obtained, and raising concerns regarding problems in the texture, such as stickiness being caused by the oils.

RELATED ART DOCUMENTS

Patent Documents

Patent Document 1: JP 3683533 B
Patent Document 2: JP 2015-124172 A

Non-Patent Documents

Non-Patent Document 1: *Shin-keshohingaku,* 2nd edition, edited by Takeo Mitsui, 2001, published by Nanzando, pp. 497-504.

SUMMARY OF THE INVENTION

Problems to be Solved by the Invention

Thus, the problem addressed by the present invention is to provide a sunscreen cosmetic that achieves high ultraviolet ray protection effects even when restricting the blended amounts of the liquid ultraviolet ray absorbing agents known as ethylhexyl methoxycinnamate and octocrylene, while also being stable, having excellent texture, and not resulting in an unnatural whiteness when applied.

Means for Solving the Problems

As a result of performing diligent research towards solving the above-mentioned problem, the present inventors discovered that a low-irritation sunscreen cosmetic that achieves a high ultraviolet ray protection effect (high SPF and high PA) even when restricting the blending of liquid ultraviolet ray absorbing agents, while simultaneously having excellent stability and texture, and not resulting in an unnatural whiteness when applied, can be obtained by combining specific solid ultraviolet ray absorbing agents and a specific oil, thereby completing the present invention.

In other words, the present invention provides a sunscreen cosmetic comprising:
(A) 0.5 to 10.0 mass % of t-butyl methoxydibenzoylmethane and/or diethylamino hydroxybenzoyl hexyl benzoate;
(B) 0.5 to 5.0 mass % of bis-ethylhexyloxyphenol methoxyphenyl triazine;
(C) 0.5 to 5.0 mass % of ethylhexyl triazone;
(D) 5 to 50 mass % of an ester oil to which the ingredients (A), (B) and (C) have a solubility, at 25° C., of 10% or more; and
(E) 1.5 to 12 mass % of an ultraviolet ray scattering agent; wherein the total blended amount of the ingredients (A), (B) and (C) is 1.5 to 15 mass % and the blended amount of ethylhexyl methoxycinnamate and octocrylene is 3 mass % or less.

Effects of the Invention

The sunscreen cosmetic of the present invention is a low-irritation sunscreen cosmetic that, even when restricting the blended amount of or not including the liquid ultraviolet ray absorbing agents known as ethylhexyl methoxycinnamate and octocrylene, highly achieves a ultraviolet ray protection effect due to a combination of specific solid ultraviolet ray absorbing agents, while simultaneously having excellent stability and texture, and not resulting in an unnatural whiteness when applied. Additionally, when a suitable amount of a powder (ultraviolet ray scattering agent) having ultraviolet ray scattering effects was added to the sunscreen cosmetic of the present invention, the unexpected effect of a synergistic improvement in the SPF was obtained. Furthermore, when the blended amounts of the ingredients (A), (B), (C) and (E) were adjusted to a specific ratio, a well-balanced ultraviolet ray protection effect was able to be obtained in the UVA and UVB wavelength ranges.

MODES FOR CARRYING OUT THE INVENTION

The sunscreen cosmetic of the present invention comprises, as essential ingredients, (A) t-butyl methoxydibenzoylmethane and/or diethylamino hydroxybenzoyl hexyl benzoate, (B) bis-ethylhexyloxyphenol methoxyphenyl triazine, and (C) ethylhexyl triazone, which are ultraviolet ray absorbing agents that are solid at ambient temperature.

(A) t-Butyl methoxydibenzoylmethane and/or diethylamino hydroxybenzoyl hexyl benzoate t-Butyl methoxydibenzoylmethane is a type of benzophenone-based ultraviolet ray absorbing agent that has a maximum absorption wavelength in the UVA range, and that has conventionally been widely used in cosmetics and the like.

The t-butyl methoxydibenzoylmethane used in the present invention may be a commercial product, an example of which is that sold by DSM Nutrition Japan under the name "Parsol 1789".

Diethylamino hydroxybenzoyl hexyl benzoate is a type of para-aminobenzoic acid (PABA)-based ultraviolet ray absorbing agent that has a maximum absorption wavelength in the UVA range.

The diethylamino hydroxybenzoyl hexyl benzoate used in the present invention may be a commercial product, an example of which is that sold by BASF Japan under the name "Uvinul A Plus".

The ingredient (A) in the sunscreen cosmetic of the present invention may contain one or both of t-butyl methoxydibenzoylmethane and diethylamino hydroxybenzoyl hexyl benzoate. The total blended amount of t-butyl methoxydibenzoylmethane and diethylamino hydroxybenzoyl hexyl benzoate is 0.5 to 10 mass %, preferably 1 to 9 mass %, more preferably 2 to 8 mass %.

(B) bis-Ethylhexyloxyphenol methoxyphenyl triazine bis-Ethylhexyloxyphenol methoxyphenyl triazine is a type of triazine-based ultraviolet ray absorbing agent that has the property of absorbing ultraviolet rays across a wide wavelength range from UVA to UVB, and is known to have high photostability.

The bis-ethylhexyloxyphenol methoxyphenyl triazine used in the present invention may be a commercial product, an example of which is that sold by BASF Japan under the name "Tinosorb S".

The blended amount of the ingredient (B) in the sunscreen cosmetic of the present invention, i.e., bis-ethylhexyloxyphenol methoxyphenyl triazine, is 0.5 to 5 mass %, preferably 0.6 to 3 mass %, more preferably 0.7 to 2 mass %.

(C) Ethylhexyl triazone

Ethylhexyl triazone is also a type of triazine-based ultraviolet ray absorbing agent that has the property of absorbing ultraviolet rays, particularly in the UVB wavelength range (maximum absorption wavelength=312 nm), and is an ultraviolet ray absorbing agent that has excellent stability.

The ethylhexyl triazone used in the present invention may be a commercial product, an example of which is that sold by BASF Japan under the name "Uvinul T150".

The blended amount of the ingredient (C) in the sunscreen cosmetic of the present invention, i.e., ethylhexyl triazone, is 0.5 to 5 mass %, preferably 0.7 to 4 mass %, more preferably 0.8 to 3 mass %.

In the sunscreen cosmetic of the present invention, the total blended amount of the ingredients (A), (B) and (C) (sometimes referred to hereinafter as the "specific solid ultraviolet ray absorbing agents") is 1.5 to 15 mass %, preferably 3 to 14 mass %, more preferably 5 to 12 mass % and most preferably 6 to 10 mass %. If this total blended amount is less than 1.5 mass %, sufficient ultraviolet ray protection performance (e.g., SPF 15 or more) cannot be obtained, and if more than 15 mass % is added, then crystal precipitation may occur.

In the sunscreen cosmetic of the present invention, it is more preferable to make adjustments so that the differences between the blended amounts of ingredients (A), (B) and (C) are within 4 mass %. For example, by setting the ratio between the blended amounts of ingredients (A), (B) and (C) so that (A):(B):(C)=23 to 8:0.7 to 2.0:0.8 to 3, and setting the difference between the blended amounts of (A), (B) and (C) so as to be within 4 mass %, a well-balanced ultraviolet ray protection effect can be obtained in the UVA and UVB wavelength ranges, and a high SPF and PA can be achieved.

(D) Ester Oil

The ingredient (D) used in the present invention is an ester oil, with the condition that the solubility, at 25° C., of each of the ingredients (A), (B) and (C) in the ester oil is at least 10% (weight/weight) (the ester oil of ingredient (D) may sometimes be referred to hereinafter as the "specific ester oil").

The specific ester oil used in the present invention may, for example, be one or more of diisopropyl sebacate, diethylhexyl succinate, glyceryl tri-2-ethylhexanoate, pentaerythrityl tetra-2-ethylhexanoate, cetyl 2-ethylhexanoate, an alkyl benzoate having 12 to 15 carbon atoms, and isononyl isononanoate. In particular, diisopropyl sebacate and/or diethylhexyl succinate is preferably used.

The blended amount of the specific ester oil (ingredient (D)) in the sunscreen cosmetic of the present invention is 5 to 50 mass %, preferably 8 to 45 mass %, more preferably 10 to 40 mass %. If the blended amount is less than 5 mass %, then the specific solid ultraviolet ray absorbing agents may partially precipitate, and even if more than 50 mass % is added, further improvements in the properties are not observed.

Additionally, in view of the stability of the cosmetic, the ratio ([(A)+(B)+(C)]/(D)) between the total blended amount of the specific solid ultraviolet ray absorbing agents (ingredients (A), (B) and (C)) and the blended amount of the specific ester oil (D) is preferably ½ or less, more preferably ⅓ or less, and even more preferably ⅕ or less.

In the sunscreen cosmetic of the present invention, sufficiently high ultraviolet ray protection performance (e.g., SPF 15 or more) is achieved by combining the specific solid ultraviolet ray absorbing agents ((A), (B) and (C)). Additionally, by also including the specific ester oil, problems such as the precipitation of the solid ultraviolet ray absorbing agents do not occur. Thus, it is possible to restrict the blended amounts of liquid ultraviolet ray absorbing agents that were added to conventional sunscreen cosmetics, i.e., ethylhexyl methoxycinnamate and octocrylene.

Accordingly, the total blended amount of ethylhexyl methoxycinnamate and octocrylene in the sunscreen cosmetic of the present invention is 3 mass % or less, preferably 2 mass % or less and more preferably 1 mass % or less. Furthermore, the sunscreen cosmetic of the present invention includes embodiments not containing ethylhexyl methoxycinnamate and octocrylene.

The sunscreen cosmetic of the present invention contains, as ingredient (E), a powder (ultraviolet ray scattering agent) that physically screens ultraviolet rays by reflection and scattering.

The ultraviolet ray scattering agent used in the present invention is not particularly limited, as long as it is a powder that can be used as an ultraviolet ray scattering agent in the field of cosmetics. Specific examples include one or more substances chosen from among titanium oxide, zinc oxide, barium sulfate, iron oxide, talc, mica, sericite, kaolin, titanated mica, Prussian blue, chromium oxide, chromium hydroxide, silica, cerium oxide and the like. In particular, it is preferable, in view of the optical properties, to use a powder having a refractive index of 1.5 or higher such as, for example, zinc oxide or titanium oxide.

The dispersibility in oil and the water resistance of an ultraviolet ray scattering agent can be improved by performing a surface hydrophobization treatment, and in the present invention, it is preferable to use an ultraviolet ray scattering agent that has been subjected to a surface hydrophobization treatment.

Examples of the surface treatment method include silicone treatments using methyl hydrogen polysiloxane, methyl polysiloxane or the like; alkyl silane treatments; fluorine treatments using perfluoroalkyl phosphate esters, perfluoroalcohols and the like; amino acid treatments using N-acyl glutamic acid or the like; and aside therefrom, lecithin treatments; metal soap treatments; fatty acid treatments; alkyl phosphate ester treatments and the like.

The ultraviolet ray scattering agent used in the present invention is not particularly limited, and it is normally preferable to use one having an average primary particle size of 100 nm or less, more preferably one that is 80 nm or less. If the average primary particle size greatly exceeds 100 nm, this tends to cause an unnatural whiteness or leave white residues.

The average primary particle size in the present invention is a value that is determined, for example, from transmission electron microscope photographs, as the arithmetic mean of the long axes and the short axes of the particles.

The particle shape of the ultraviolet ray scattering agent is not particularly limited, and it may be in the form of primary particles, or they may be coagulated to form secondary aggregates. Additionally, there are no particular limitations as to the shape, which may be spherical, elliptical, crushed or the like.

The blended amount of the ultraviolet ray scattering agent in the sunscreen cosmetic of the present invention is 1.5 to 12 mass %, preferably 2 to 10 mass %, and most preferably 2 to 6 mass %. If the blended amount is less than 1.5 mass %, then the resulting ultraviolet ray protection effect is not sufficient, and if more than 12 mass % is added, then the whiteness becomes noticeable when applied, and there may be a powdery sensation when used.

In the sunscreen cosmetic of the present invention, a high ultraviolet ray protection effect is obtained by blending the ingredients (A), (B), (C) and (E), and a high SPF can be achieved by adjusting the total blended amount of the ingredients (C) and (E) to be 8 mass % or more.

In addition to the essential ingredients, which are the specific solid ultraviolet ray absorbing agents ((A), (B) and (C)), the specific ester oil (D) and the ultraviolet ray scattering agent (E), the sunscreen cosmetic of the present invention may contain other optional ingredients that may normally be added to sunscreen cosmetics, within a range not inhibiting the effects of the present invention.

Although the other optional ingredients are not particularly limited, they include, for example, ultraviolet ray absorbing agents (excluding ethylhexyl methoxycinnamate and octocrylene) other than the specific solid ultraviolet ray absorbing agents. By adding these, it is possible to further improve the ultraviolet ray protection performance in the UVA and/or the UVB range.

The ultraviolet ray absorbing agents other than the specific solid ultraviolet ray absorbing agents ((A), (B) and (C)) may be chosen from among those that are normally used in cosmetics, and are not particularly limited. Examples include one or more substances chosen from among para-aminobenzoic acid derivatives, salicylic acid derivatives, cinnamic acid derivatives, β,β-diphenyl acrylate derivatives, benzophenone derivatives, benzylidene camphor derivatives, phenyl benzimidazole derivatives, triazine derivatives, phenyl benzotriazole derivatives, anthranil derivatives, imidazoline derivatives, benzalmalonate derivatives, 4,4-diaryl butadiene derivatives and the like.

Other optional ingredients include, but are not limited to, water-soluble polymers, oil-soluble polymers, waxes, alcohols, hydrocarbon oils, fatty acids, higher alcohols, fatty acid esters, silicone oils, surfactants, powder components other than ultraviolet ray scattering agents, pharmaceutical agents and the like.

Examples of water-soluble polymers include homopolymers or copolymers of 2-acrylamido-2-methylpropane sulfonic acid (hereinafter abbreviated to "AMPS"). The copolymers are copolymers with comonomers such as vinyl pyrrolidone, acrylic acid amides, sodium acrylate and hydroxyethyl acrylate. In other words, examples include AMPS homopolymers, vinyl pyrrolidone/AMPS copolymers, dimethyl acrylamide/AMPS copolymers, acrylic acid amide/AMPS copolymers, sodium acrylate/AMPS copolymers and the like.

Further examples include carboxyvinyl polymers, ammonium polyacrylate, sodium polyacrylates, sodium acrylate/alkyl acrylate/sodium methacrylate/alkyl methacrylate copolymers, carrageenan, pectin, mannan, curdlan, chondroitin sulfate, starch, glycogen, gum arabic, sodium hyaluronate, tragacanth gum, xanthan gum, mucoitin sulfate, hydroxyethyl guar gum, carboxymethyl guar gum, guar gum, dextran, keratosulfate, locust bean gum, succcinoglucan, chitin, chitosan, carboxymethyl chitin, agar and the like.

Examples of the oil-soluble polymer include trimethylsiloxysilicate, alkyl-modified silicone, polyamide-modified silicone, dimethicone cross-polymers, (dimethicone/vinyl dimethicone) cross-polymers, poylmethylsilsesquioxane and the like.

Examples of waxes include beeswax, candelilla wax, carnauba wax, lanolin, liquid lanolin, jojoba wax and the like.

Examples of alcohols include lower alcohols such as ethanol and isopropanol, and polyhydric alcohols such as ethylene glycol, propylene glycol, 1,3-butylene glycol, dipropylene glycol and polybutylene glycol.

Examples of hydrocarbon oils include liquid paraffin, ozokerite, squalane, pristane, paraffin, ceresin, squalane, vaselin, microcrystalline wax, polyethylene wax, Fischer-Tropsch waxes and the like.

Examples of fatty acids include lauric acid, myristic acid, palmitic acid, stearic acid, behenic acid, arachidonic acid and the like.

Examples of higher alcohols include lauryl alcohol, myristyl alcohol, cetyl alcohol, stearyl alcohol, behenyl alcohol, arachyl alcohol, batyl alcohol, chimyl alcohol, carnaubyl alcohol, ceryl alcohol, corianyl alcohol, myricyl alcohol, lacceryl alcohol, elaidyl alcohol, isostearyl glycyerl ether, octyl alcohol, triacontyl alcohol, selachyl alcohol, cetostearyl alcohol, oleyl alcohol, lanolin alcohol, hydrogenated lanolin alcohol, isostearyl alcohol, hexyl decanol, octyl decanol and the like.

Examples of silicone oils include methyl polysiloxane, octamethyl siloxane, decamethyl tetrasiloxane, methyl hydrogen polysiloxane, methyl phenyl polysiloxane, hexamethyl cyclotrisiloxane, octamethylcyclotetrasiloxane, decamethylcyclopentasiloxane and the like. Preferable examples include octamethylcyclotetrasiloxane, decamethylcyclopentasiloxane and the like.

Examples of surfactants include anionic, cationic, nonionic or amphoteric surfactants, including silicone-based or hydrocarbon-based surfactants.

Examples of powder ingredients other than ultraviolet ray scattering agents (ingredient E) include nylon or acrylic polymer spherical powders, silica powders, silicone powders, metal oxide powders that have been surface-treated with surface treating agents not containing metals, and the like.

Examples of pharmaceutical agents include L-ascorbic acid and derivative salts thereof, glycyrrhizic acid and derivatives thereof such as dipotassium glycyrrhizate and monoammonium glycyrrhizate, glycyrrhetinic acid and derivatives thereof such as stearyl glycyrrhetinate, allantoin, tranexamic acid and derivative salts thereof, alkoxysalicylic acid and derivative salts thereof, glutathione and derivative salts thereof, allantoin, azulene and the like.

The sunscreen cosmetic of the present invention may be provided in the form of an oil-in-water emulsion cosmetic, a water-in-oil emulsion cosmetic or an oil-based cosmetic. Specific formats include formats such as sunscreen lotions and sunscreen creams, which may be manufactured using conventional methods that are appropriate for each format.

EXAMPLES

Herebelow, the present invention will be described in further detail by giving examples, but the present invention is not to be construed as being limited thereto. Where not specifically noted, amounts are indicated in mass % with respect to the system in which the ingredient is contained.

Samples of emulsified sunscreen cosmetics were prepared with the formulations indicated in Table 1 and Table 2 below. Next, the samples of the formulated examples were evaluated as to (1) SPF value, (2) crystal precipitation, and (3) whiteness when applied, as indicated below. The evaluation results are also shown in Table 1.

(1) SPF

The sun protection factor (SPF) was measured using an SPF measuring device, "SPF MASTER" (registered trademark) (Shiseido).

(2) Crystal Precipitation

Observations of the sample, which was left at 0° C., were made through a polarizing microscope in order to visually determine whether or not crystal precipitation could be observed.

A: No crystal precipitation observed.
B: Crystal precipitation observed.

(3) Whiteness when Applied

Female panelists (ten) applied samples of each of the examples and comparative examples, and evaluated them for whiteness on the basis of the following evaluation criteria.

(Evaluation)
A: 3 or fewer responded that the whiteness after application was unacceptable.
B: 4 or more responded that the whiteness after application was unacceptable.

TABLE 1

|  | Comp. Ex. 1 | Comp. Ex. 2 | Comp. Ex. 3 | Comp. Ex. 4 | Comp. Ex. 5 |
|---|---|---|---|---|---|
| Water | 18.3 | 28.3 | 25.8 | 25.8 | 28.3 |
| Disteardimonium hectorite | 0.2 | 0.2 | 0.2 | 0.2 | 0.2 |
| PEG-9 polydimethylsiloxyethyl dimethicone | 1.5 | 1.5 | 1.5 | 1.5 | 1.5 |
| Triethylhexanoin | 10 | 10 | 10 | 10 | 10 |
| Diisopropyl sebacate | — | — | — | 10 | 10 |
| Diethylhexyl succinate | — | — | — | 10 | 10 |
| Pentaerythrityl tetraethylhexanoate | 10 | 10 | 10 | 10 | 10 |
| PPG-3 dipivalate | 10 | 10 | 10 | 10 | 10 |
| Cyclomethicone | 10 | 10 | 22.5 | 12.5 | 15 |
| Dimethicone | 10 | 10 | 10 | — | — |
| Ethylhexyl methoxycinnamate | 10 | — | — | — | — |
| Octocrylene | 10 | — | — | — | — |
| bis-Ethylhexyloxyphenol methoxyphenyl triazine | — | — | 1 | 1 | — |
| t-Butyl methoxydibenzoylmethane | 5 | — | 5 | 5 | — |
| Ethylhexyl triazone | — | — | 2 | 2 | — |
| Diethylaminohydroxybenzoyl hexyl benzoate | — | — | 2 | 2 | — |

TABLE 1-continued

|  | Comp. Ex. 1 | Comp. Ex. 2 | Comp. Ex. 3 | Comp. Ex. 4 | Comp. Ex. 5 |
|---|---|---|---|---|---|
| Triethoxycaprylylsilane-treated titanium oxide | 5 | 10 | — | — | 5 |
| Dimethicone-treated zinc oxide | — | 10 | — | — | — |
| SPF MASTER | 22 | 19 | 6 | 6 | 6 |
| Crystal precipitation | A | A | B | A | A |
| Whiteness | A | B | A | A | A |

TABLE 2

|  | Comp. Ex. 6 | Comp. Ex. 7 | Ex. 1 | Ex. 2 | Ex. 3 | Ex. 4 |
|---|---|---|---|---|---|---|
| Water | 25.8 | 25.8 | 25.8 | 43.3 | 43.3 | 46.3 |
| Disteardimonium hectorite | 0.2 | 0.2 | 0.2 | 0.2 | 0.2 | 0.2 |
| PEG-9 polydimethylsiloxyethyl dimethicone | 1.5 | 1.5 | 1.5 | 1.5 | 1.5 | 1.5 |
| Triethylhexanoin | 10 | 10 | 10 | 10 | 10 | 10 |
| Diisopropyl sebacate | 10 | 10 | 10 | 10 | 10 | 10 |
| Diethylhexyl succinate | 10 | 10 | 10 | 10 | 10 | 10 |
| Pentaerythrityl tetraethylhexanoate | 10 | 10 | 10 | — | — | — |
| PPG-3 dipivalate | 2.5 | 10 | 10 | — | — | — |
| Cyclomethicone | 5 | 11.5 | 7.5 | 10 | 10 | 10 |
| Dimethicone | — | — | — | — | — | — |
| Ethylhexyl methoxycinnamate | — | — | — | — | — | — |
| Octocrylene | — | — | — | — | — | — |
| bis-Ethylhexyloxyphenol methoxyphenyl triazine | 1 | 1 | 1 | 1 | 1 | 1 |
| t-Butyl methoxydibenzoylmethane | 5 | 5 | 5 | 5 | 5 | 5 |
| Ethylhexyl triazone | 2 | 2 | 2 | 2 | 2 | 2 |
| Diethylaminohydroxybenzoyl hexyl benzoate | 2 | 2 | 2 | 2 | 2 | 2 |
| Triethoxycaprylylsilane-treated titanium oxide | 15 | 1 | 5 | 5 | — | 2 |
| Dimethicone-treated zinc oxide | — | — | — | — | 5 | — |
| SPF MASTER | 35 | 7 | 22 | 21 | 19 | 15 |
| Crystal precipitation | A | A | A | A | A | A |
| Whiteness | B | A | A | A | A | A |

As is clear from the results shown in Table 1, a high ultraviolet ray protection effect of SPF=22 was obtained in a conventional sunscreen cosmetic (Comparative Example 1) containing ethylhexyl methoxycinnamate and octocrylene, which are liquid ultraviolet ray absorbing agents. In Comparative Example 2, in which all of the ultraviolet ray absorbing agents in Comparative Example 1 were substituted with ultraviolet ray scattering agents, approximately the same level of ultraviolet ray protection effects (SPF=19) were obtained, but the unnatural whiteness at the time of application was of an unacceptable level. On the other hand, when the liquid ultraviolet ray absorbing agents in Comparative Example 1 were replaced with solid ultraviolet ray absorbing agents, crystal precipitation occurred (Comparative Example 3), and although the crystal precipitation was able to be prevented by adding a specific ester oil, sufficient ultraviolet ray protection effect was not obtained (Comparative Example 4).

The results indicated in Table 2 show that, by adding 5 mass % of an ultraviolet ray scattering agent to Comparative Example 4, it is possible to obtain about the same level of ultraviolet ray protection effects (SPF=22) as in conventional products (Comparative Example 1), even without including a liquid ultraviolet ray absorbing agent (Example 1). While this Example 1 has a composition combining Comparative Example 4 and Comparative Example 5 in Table 1, the synergistic improvement in the SPF relative to Comparative Example 4 (SPF=6) and Comparative Example 5 (SPF=6) was a surprising effect. A "synergistic improvement" refers to an effect in which a combination of a composition containing A (with the effect a) and a composition containing B (with the effect b) yields effects exceeding the simple sum (a+b) of the effects of A and B alone.

Comparative Example 6 shown in Table 2 contains an ultraviolet ray scattering agent in excess of the prescribed range (1.5 to 12 mass %) in the present invention, as a result of which the whiteness at the time of application was of an unacceptable level. Conversely, sufficient ultraviolet ray protection effects were not obtained (SPF=7) in Comparative Example 7, in which the blended amount of the ultraviolet ray scattering agent was less than the prescribed range.

Example 2, in which some of the oil-based medium in Example 1 was replaced with water, and Examples 3 and 4, in which the blended amounts and types of the ultraviolet ray scattering agents in Example 2 were changed within the range of the present invention, were satisfactory in terms of the ultraviolet ray protection effect (SPF), the stability and texture, and the appearance.

With the exception of Comparative Example 1, the samples listed in Tables 1 and 2 did not cause irritation even when applied to the face.

Furthermore, samples of emulsified sunscreen cosmetics were prepared with the formulations indicated in Table 3 below. Next, the samples of the formulated examples were evaluated as to (1) SPF value, and (2) PA value, as indicated below. The evaluation results are also shown in Table 3.

(1) SPF

The sun protection factor (SPF) was measured using an SPF measuring device, "SPF MASTER" (registered trademark) (Shiseido).

(2) PA

The protection grade of UVA (PA), was measured using a benchtop xenon photostability sensor, "Atlas SUNTEST XLS+" (Toyoseiki), and a spectrophotometer, "U-4100" (Hitachi). An "A" indicates that the PA computed by using the aforementioned devices was +++ or higher, and a "B" indicates that the PA was ++ or lower.

TABLE 3

|  | Ex. 5 | Ex. 6 | Ex. 7 | Ex. 8 |
|---|---|---|---|---|
| Water | 22.3 | 22.3 | 22.3 | 21.3 |
| Disteardimonium hectorite | 0.2 | 0.2 | 0.2 | 0.2 |
| PEG-9 polydimethylsiloxyethyl dimethicone | 1.5 | 1.5 | 1.5 | 1.5 |
| Triethylhexanoin | 10 | 10 | 10 | 10 |
| Diisopropyl sebacate | 10 | 10 | 10 | 10 |
| Diethylhexyl succinate | 10 | 10 | 10 | 10 |
| Pentaerythrityl tetraethylhexanoate | 10 | 10 | 10 | 10 |
| Isopropyl myristate | 10 | 10 | 10 | 10 |
| Cyclomethicone | 15 | 15 | 15 | 15 |
| bis-Ethylhexyloxyphenol methoxyphenyl triazine | 0.5 | 2 | 1 | 2 |
| Ethylhexyl triazone | 5 | 2 | 3 | 2 |
| Diethylaminohydroxybenzoyl hexyl benzoate | 0.5 | 2 | 2 | 2 |
| Triethoxycaprylylsilane-treated titanium oxide | 5 | 5 | 5 | 6 |
| SPF MASTER | 27 | 14 | 18 | 20 |
| PA | B | A | A | A |

The sunscreen cosmetics (Examples 7 and 8) in which the differences between the blended amounts of ingredient (A) and ingredient (C) and the blended amounts of ingredient (B) and ingredient (C) were 4 mass % or less, and the total blended amount of the (C) ethylhexyl triazone and the (E) ultraviolet ray scattering agent was 8 mass % or more achieved a good balance of very excellent protection effects, namely an SPF of 15 or higher and a PA of +++ or higher, across a wide wavelength range from UVA to UVB.

On the other hand, in a sunscreen cosmetic (Example 5) in which the differences between the blended amounts of ingredient (A) and ingredient (C) and the blended amounts of ingredient (B) and ingredient (C) exceeded 4 mass %, the SPF was an extremely high value (27), but the PA was ++.

Additionally, in a cosmetic (Example 6) in which the total blended amount of the (C) ethylhexyl triazone and the (E) ultraviolet ray scattering agent was less than 8 mass %, a PA of +++ or higher was obtained, but the SPF value was slightly lower. In other words, it was discovered that, if it is important to obtain a balance of ultraviolet ray protection performance in the UVA and UVB ranges, then it is preferable to set the differences between the blended amounts of ingredient (A) and ingredient (C) and the blended amounts of ingredient (B) and ingredient (C), and the total blended amount of ingredient (C) and ingredient (E), so as to be within the above-mentioned ranges.

The invention claimed is:

1. A sunscreen cosmetic, comprising:
   (A) 0.5 to 10.0 mass % of at least one of t-butyl methoxydibenzoylmethane and diethylamino hydroxybenzoyl hexyl benzoate;
   (B) 0.5 to 5.0 mass % of bis-ethylhexyloxyphenol methoxyphenyl triazine;
   (C) 0.5 to 5.0 mass % of ethylhexyl triazone;
   (D) 5 to 50 mass % of an ester oil; and
   (E) 1.5 to 12 mass % of an ultraviolet ray scattering agent having a refractive index of 1.5 or higher;
   wherein:
   at least 10% of a total blended amount of said (A), (B) and (C) is soluble in (D) said ester oil at 25° C.;
   a total blended amount of said (A), (B) and (C) is 1.5 to 15 mass % in said sunscreen cosmetic; and
   a total blended amount of ethylhexyl methoxycinnamate and octocrylene is 3 mass % or less;
   with the proviso that if the difference between the blended amounts of the ingredients (A) and (C) and the difference between the blended amounts of the ingredients (B) and (C) are both 4 mass % or less, then the total blended amount of ingredients (C) and (E) is 8 mass % or more.

2. The sunscreen cosmetic, according to claim 1, wherein: the (D) ester oil comprises at least one of diisopropyl sebacate and diethylhexyl succinate.

3. The sunscreen cosmetic, according to claim 1, wherein: said sunscreen cosmetic does not contain ethylhexyl methoxycinnamate or octocrylene.

4. The sunscreen cosmetic, according to claim 1, wherein: the (E) ultraviolet ray scattering agent is a zinc oxide powder or a titanium oxide powder.

5. The sunscreen cosmetic, according to claim 1, wherein: said sunscreen cosmetic has a sun protection factor (SPF) of 15 or higher.

* * * * *